(12) United States Patent
Conlan

(10) Patent No.: US 6,293,150 B1
(45) Date of Patent: Sep. 25, 2001

(54) MOTION SENSOR AND METHOD OF MAKING SAME

(75) Inventor: Robert W. Conlan, Niceville, FL (US)

(73) Assignee: Precision Control Design, Fort Walton Beach, FL (US)

( * ) Notice: Subject to any disclaimer, the term of this patent is extended or adjusted under 35 U.S.C. 154(b) by 0 days.

(21) Appl. No.: 09/453,331

(22) Filed: Dec. 2, 1999

(51) Int. Cl.[7] .............................. G01P 3/00; A61B 5/00
(52) U.S. Cl. .............................. 73/536; 600/595
(58) Field of Search .................... 73/504.15, 536, 73/540, 545, 535, 542, 862.621, 862.627, 862.629, 862.632, 862.634, 862.636, 862.637, 862.639; 600/595, 587, 493, 503

(56) References Cited

U.S. PATENT DOCUMENTS 5,014,555 * 5/1991 Haines ..................................... 73/536
5,197,489 * 3/1993 Conlan .................................. 128/782

FOREIGN PATENT DOCUMENTS

2129592 * 5/1984 (GB) .

* cited by examiner

*Primary Examiner*—Helen Kwok
(74) *Attorney, Agent, or Firm*—Cook, Alex, McFarron, Manzo, Cummings & Mehler

(57) ABSTRACT

A motion sensor for monitoring the activity of a body in motion includes a pair of force detecting sensors capable of detecting both magnitude and direction of an applied force. These sensors are configured to enable translational or rotational motion resulting from travel in a vehicle to be suppressed from any general motion signal leaving only a rotational or translational component. The active compensation of an electrical circuit is provided to aid in the calibration of a non-ideal sensor pair and reduce the leakage of translational motion into rotational motion or rotational motion into translational motion due to any differences between the pair.

12 Claims, 5 Drawing Sheets

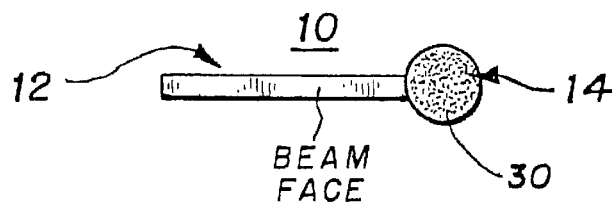
FIG. 1a
(PRIOR ART)
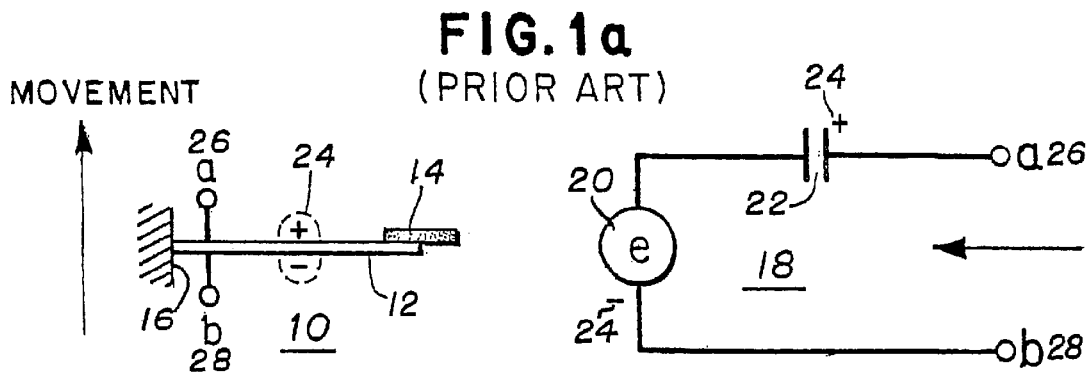
FIG. 1b
(PRIOR ART)
FIG. 1c
(PRIOR ART)
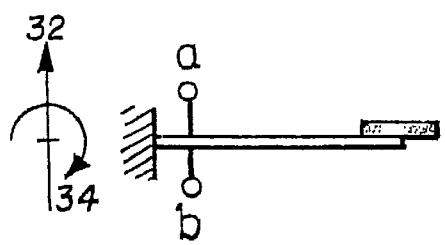
FIG. 2a
(PRIOR ART)
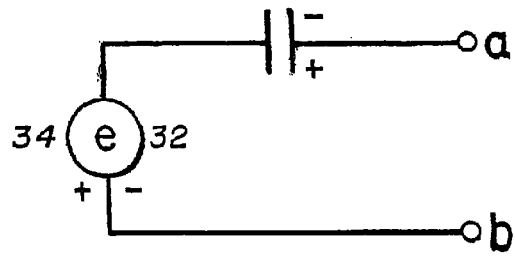
FIG. 2b
(PRIOR ART)
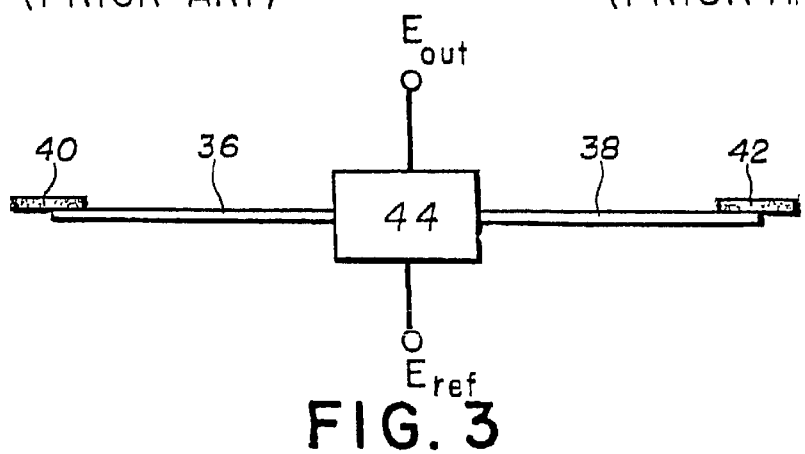
FIG. 3

MOTION SENSOR AND METHOD OF MAKING SAME

BACKGROUND OF THE INVENTION

The present invention relates generally to motion sensors for monitoring the activity of a body in motion. More particularly, the invention relates to apparatus, systems and methods by which translational or rotational motion may be suppressed from any general motion signal leaving only a rotational or translational component.

Motion sensors have been applied to a plethora of applications, one of the most important of which being research instruments for a variety of medical studies concerned with the human body. Although the present invention may be described with respect to human activity monitors, or actigraphs, it will be appreciated that the motion sensor described herein is in no way intended to be limited to such an application. In fact, it will be understood that this new type of motion sensor may be applied to any application which may necessitate the suppression of the translational or rotational motion from a general motion signal leaving only a rotational or translational component.

The observation of body movement can provide much information useful to physicians and researchers. For example, by observing movement in a subject, the occurrence and length of natural phenomenon, such as wakefulness, rest, and sleep can be determined. By observing the nature of a subject's movement, the occurrence and severity of disorders and the effects of drugs or other therapy can be assessed. In many cases quantification of the subject's movement is preferred so that the movement pattern of one subject can be compared with the movement pattern of others.

Direct visual observations of body movement are labor intensive, time consuming and tedious. Moreover, direct visual observations provide only a limited range of qualitative information, such as subjective descriptions of a subject's visually perceptible movements. Little, if any, quantification in readily comparable values, such as degree, strength, and/or violence of a subject's activity, and no information, either qualitative or quantitative, of a subject's visually imperceptible movements is obtained. Furthermore, the value of qualitative information obtained by directly observing a subject is subject to question as such observations themselves may cause the subject to become conscious of and thereby alter his or her movements.

Activity monitors, and in particular, actigraphs have been developed for observing and quantifying certain aspects of movements without the involvement of an observer. In its earliest manifestation, the actigraph was primarily a wrist worn sleep research tool, and much of modern actigraph design philosophy has evolved from this application. Today, however, actigraphs are frequently used in other research which involves hyperactivity, nocturnal tremors, circadian behavior (i.e. shift work) and Parkinson's Disease.

However, such actigraphs had disadvantages which limited their usefulness. For example, it was realized that measurement of human activity could not be accomplished if the subject was moving on a platform which was itself moving relative to the earth. Consequently, actigraphs could not be utilized effectively on a human involved in driving, flying, boating or riding on a train for example. In particular, it was discovered, at least in so far as road vehicles are concerned, that frequency range and statistics were not sufficiently different from human characteristics to allow an actigraph to separate two overlapping signals. Furthermore, it was found that road vehicle motion was found to be 10 to 100 times greater in amplitude than that produced by a riding human.

In recent years the need for a new type of actigraph capable of sensing human activity in a moving vehicle reached a new level of importance as several independent industries have become interested at the same time. For example, sleep aboard military aircraft became an important topic because transporting combat soldiers during a crisis requiring urgent deployment often requires rest/sleep onboard the aircraft. Perhaps most importantly, the Federal Highway Administration began inquiring about technology that could determine how well a truck driver sleeps in a truck berth under various scenarios. Such as, while the truck is idling, as in the case with a single crew member and while the truck is moving, as in the case with a two man crew. Others had now become interested as well primarily due to the fact that effectiveness and personal safety are determined to a great extent upon an individual's sleep quality and duration.

In view of the afore-mentioned needs and the shortcomings of the prior art, it is therefore a general object of the present invention to provide a new type of motion sensor for monitoring the activity of a body in motion.

It is another object of the present invention to provide an apparatus, system and method by which translational or rotational motion may be suppressed from any general motion signal leaving only a rotational or translational component.

Still another object of the present invention is to provide a motion sensor capable of sensing human activity in a moving vehicle.

Yet another object of the present invention is to provide a motion sensor capable of assessing sleep and performance of humans subject to long term mechanical vibrations in the work place.

Still yet another object of the present invention is to provide a motion sensor capable of recording short duration time records of important movements.

These and other objects, features and advantages of the present invention will be clearly understood through a consideration of the following detailed description.

SUMMARY OF THE INVENTION

The invention is directed to a motion sensor for monitoring the activity of a body in motion having a pair of force detecting sensors capable of deleting both the magnitude and direction of an applied force. These sensors may be in the form of beams attached at one end to a mount and having at their other end a small proof mass. When the sensor is put into motion, the beams provide a cantilever effect through a voltage/capacitance effect and produce both translational and rotational motion components. A means of connecting these effects enables the cancellation of the rotational or translational counterpart.

BRIEF DESCRIPTION OF THE DRAWINGS

The features of the present invention which are believed to be novel are set forth with particularity in the appended claims. The invention, together with the further objects and advantages thereof, can best be understood by reference to the following description taken in conjunction with the accompanying drawings, in the several figures of which like reference numerals identify like elements, and in which:

FIG. 1a is a top plan view of a standard activity sensor of the prior art.

FIG. 1b is a side view of the sensor of FIG. 1a.

FIG. 1c is a schematic of the equivalent electrical circuit of the sensor of FIG. 1a.

FIG. 2a is a side view of the sensor of FIG. 1a showing the direction of the translational and rotational motion components.

FIG. 2b is a schematic of the equivalent electrical circuit of the sensor of FIG. 2a.

FIG. 3 is a side view of the basic concept of the motion sensor of the present invention showing a module to symbolize the multiple possible wiring arrangements.

FIG. 4c is a vector component diagram of the motion sensor of FIG. 4a.

FIG. 5b is the equivalent circuit model of the motion sensor of FIG. 5a.

FIG. 7b is the equivalent circuit model of the motion sensor of FIG. 7a.

FIG. 8b is the equivalent circuit model of the motion sensor of FIG. 8a.

FIG. 9b is the equivalent circuit model of the motion sensor of FIG. 9a.

DESCRIPTION OF THE PREFERRED EMBODIMENT

Figure 4A:
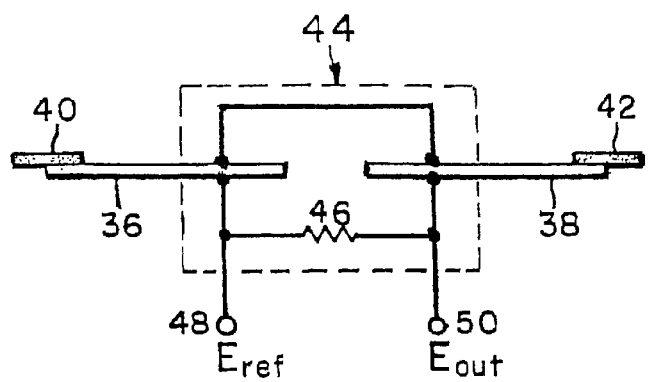
FIG. 4a is a side view of a wiring arrangements of the motion sensor of FIG. 3.

Referring to the Figures, and particularly to FIGS. 1a–1c, the standard activity sensor 10 of the prior art is an off the shelf piezoelectric bimorph beam 12 which has a small proof mass 14 attached to one end. This beam 12 is mounted at its other end 16 (FIG. 1b) to provide the necessary cantilever effect whereby the essential high sensitivity and conservation of power is achieved as well as the capability to operate in the absence of a gravitational field.

The equivalent electrical circuit 18 to this cantilever piezoelectric bimorph beam 12 comprises a voltage source 20 in series with a capacitor 22 as shown in FIG. 1c. The sign convention 24 as shown in FIGS. 1b and 1c were chosen so that when the top fibers of the beam 12 are "stretched" (when the beam moves downwards), the top of the beam 12 is more positive than the bottom. The top and bottom of the beam 12 are preferably comprised of thin layers of plated silver while the interior is a ceramic material preferably of lead titanate. Thus, it appears that the voltage source is between the two silver plates which form the capacitor electrodes.

The equivalent circuit of FIG. 1c correctly models the reaction of the beam 12 and its cooperating sign convention 24. For example, when the movement direction reverses, the beam 12 bends upward and the voltage polarity reverses. Output from the beam 12 is only available across nodes a & b (26, 28), and only alternating movement can be detected because the capacitor blocks direct current. In other words, this type of sensor cannot detect gravity. Additionally, this beam is only sensitive to movement or movements components perpendicular to the flat face 30 of the mass, thus the so-called "single axis motion detector."

Arbitrary motion and thus virtually any human motion consists of translational motion ("TM") 32 and rotational motion ("RM") 34 components. As RM and TM always occur simultaneously for human activity, they can be resolved about the beam restraint as shown in FIG. 2a and equivalently shown as the electrical circuit of FIG. 2b. The opposite sign conventions of FIG. 2b illustrates that the RM and TM voltages are 180 degrees out of phase. One of these voltages will typically be dominant and thus determine the net polarity of the voltage source. However, if the rotational direction changes from clockwise to counterclockwise, then RM voltage polarity changes, and thus RM and TM would be exactly in phase.

Not only do RM and TM coexist with respect to human motion, but they start and stop together. While it may be possible to have more cycles of RM relative to TM, or vice a versa, it must always be true that both start and stop at the beginning and ending of wrist activity. That said, if only the human wrist translational movement is canceled by a new type of sensor, the remaining rotational piece will preserve the fact that the wrist moved.

Where as human wrist motion is rich in both translational and rotational components, road vehicles (cars and trucks) don't measurably pitch or rock and therefore lack such rotational components. Any vehicle that pitches or rocks is decideably uncomfortable and such problems are either fixed at the vehicular design phase or with after market suspension solutions. In fact, road vehicles are especially stiff to angular oscillations and it has been the working of the suspension system which creates vertical oscillations that affected these prior art actigraphs. Therefore, if these road induced mechanical oscillations could be canceled by the new type of motion sensor of the present invention, then only human rotational motion would remain, which is sufficient for the aforementioned biological applications.

The present invention is directed to a motion sensor for monitoring the activity of a body in motion by a pair of force detecting sensors capable of detecting both the magnitude and the direction of applied force. Typical examples of this type of sensor include metal foil strain gages configured as a resistive bridge, solid state strain gages configured as a capacitive bridge and a piezoelectric bimorph element with a load resistor. These sensors are often set up to measure force in one direction and are called single axis sensors. Therefore, only the component of force parallel to this direction will be sensed. When configured as a matched pair, it is then possible to cancel pure translational motion while preserving pure rotational motion or to cancel pure rotational motion while preserving pure translational motion. For a linear sensor, superposition applies and, therefore, any general motion consisting of rotational and translational can be split into rotation alone or translation alone.

The design of this matched pair of detecting sensors may best be engineered in the long term through a micromachining process. Such a process will enable the fabrication of these sensors with great accuracy. In other words, a solid state (silicon based) capacitive type sensor which can be machined into a microchip, including the electronics, or a single chip product. However, at the time of this writing, the preferred embodiment remains the piezoelectric bimorph beam design. It will be understood that the scope of the present invention shall not be limited to that as described as the preferred embodiment herein and that such embodiment is provided for explanation and enablement purposes.

Therefore, the concept of the preferred embodiment of the present invention may most generally be described with respect to FIG. 3 which basically shows two beams 36, 38 rigidly connected together so they move as a unit. It is not necessary that the beams be aligned co-linearly as shown in FIG. 3, only that the two masses 40, 42 are spaced apart. The "module" 44 contains interconnecting wiring and illustrates that the new type of sensor of the present invention is a two terminal device. As will be discussed, this configuration provides for a generic sensor which can eliminate translational motion or rotational motion.

Figure 5A:
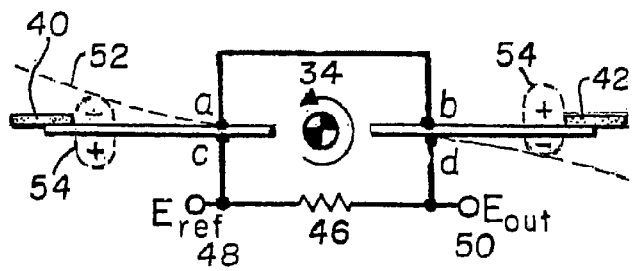
FIG. 5a is a side view showing the resultant effects of the motion sensor of FIG. 4a if moving in pure rotation.
Figure 5B:
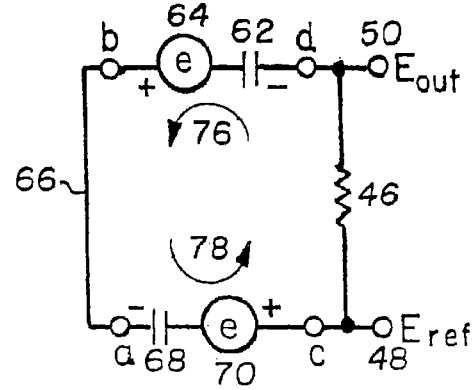
Figure 6:
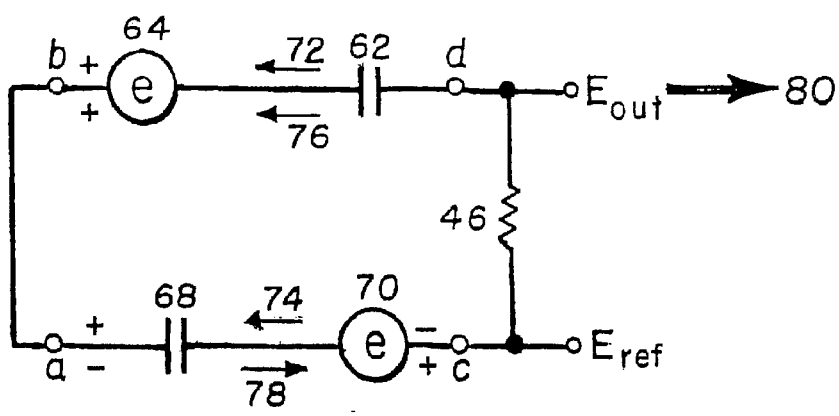
FIG. 6 is the equivalent circuit model of the wiring arrangement of FIG. 4a for any general motion.

Presently, there are at least four (4) ways to connect beams 36,38 via module 44 to achieve the desired result. Although there may certainly be other possible configurations, those to be described appear to be the most straightforward and easiest to apply. The first and simplest of which is illustrated in FIGS. 4–6. The circuit within module 44 of FIG. 4a includes a resistor 46 which is necessary to close the circuit and permit current flow. With $E_{ref}$(48) typically fixed at 1.2 volts in one realization, the circuit output $E_{out}$(50) will swing above or below $E_{ref}$(48) according to how the beams move. For example, if the beams 36,38 are moved in pure translation 32, the resulting deflections or bend line 52 and consequential polarities 54 would appear as illustrated in FIG. 4b. The upward movement results in both masses 40,42 deflecting downward in phase, and that the generated voltages will have the polarity shown. The direction of movement relative to the beam axis is not important, because only the component perpendicular to the flat beam face induces a voltage response, as illustrated in FIG. 4c. Thus, if the movement is in the direction of vector 56 of FIG. 4c, then the vector component 58 relative to the beam axis will have no effect, while the vector component 60 perpendicular to the beam provides all of the TM effect and voltage response.

Figure 4C:
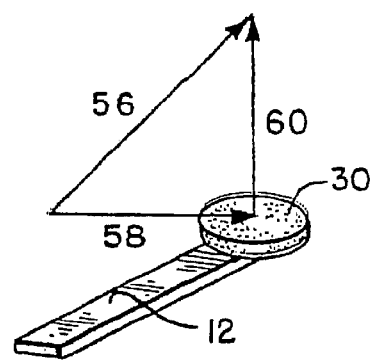
Figure 4B:
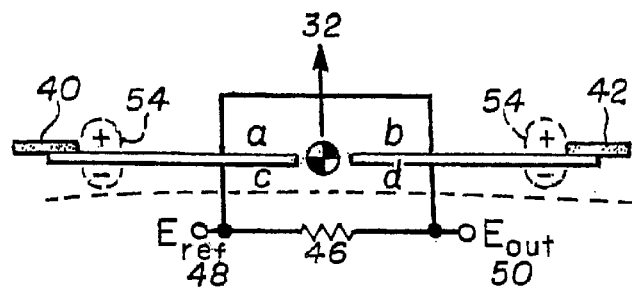
FIG. 4b is a side view showing the resultant effects of the motion sensor of FIG. 4a if moving in pure translation.
Figure 4D:
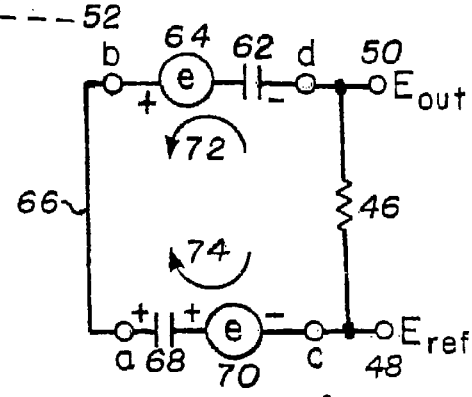
FIG. 4d is an equivalent circuit model of the motion sensor of FIGS. 4a–c.

The equivalent circuit model of FIGS. 4a–c is shown in FIG. 4d. Between nodes d and b, the beam 38 is replaced by its equivalent circuit, including capacitor 62 and voltage source 64. Across nodes b and a there is only a connection 66. From nodes a to c, again the beam 36 is replaced by its electrical circuit, including capacitor 68 and voltage source 70. The upper branch of this circuit model circulates current counterclockwise 72, while the lower branch circulates current clockwise 74. Assuming pure TM and that the two beams (36,38) and masses (40,42) are identical the resulting currents (72,74) are equal magnitude opposite direction, thus there is no net current passing through the resistor 46. This means that $E_{out}=E_{ref}$, in other words there is no activity signal and $E_{ref}$ is merely an offset voltage to be referred to as a "virtual" ground. Therefore, the circuit of FIG. 4d cancels translation.

Assuming pure rotation, the two beams (36,38) move out of phase. The resulting beam deflections or bend line 52 and consequential polarities 54 would appear as illustrated in FIG. 5a. The equivalent circuit model of FIG. 5a is shown in FIG. 5b. The model circuit of FIG. 5b comprises the same elements as the circuit of FIG. 4d, except for the difference in polarity and, thus, current flow. The upper branch of the circuit of FIG. 5b circulates current counterclockwise 76, while the lower branch also circulates current counterclockwise 78. Thus, net current flows through the resistor 46 and the voltage output 50 will oscillate with oscillating rotational movement.

The circuit model of the first configuration of the preferred embodiment of the present invention for any general motion, that in which RM and TM occur simultaneously, is illustrated in FIG. 6. Because the circuit is linear, superposition applies and the circuit behaves exactly as described for a composite signal. In particular, the circuit elements of FIGS. 4d and 5b have been superimposed. The resulting TM current flows 72 and 74, along with the resulting RM current flows 76 and 78 cancels TM and passes 2RM (80) or 76 plus 78 out through $E_{out}$.

Figure 7A:
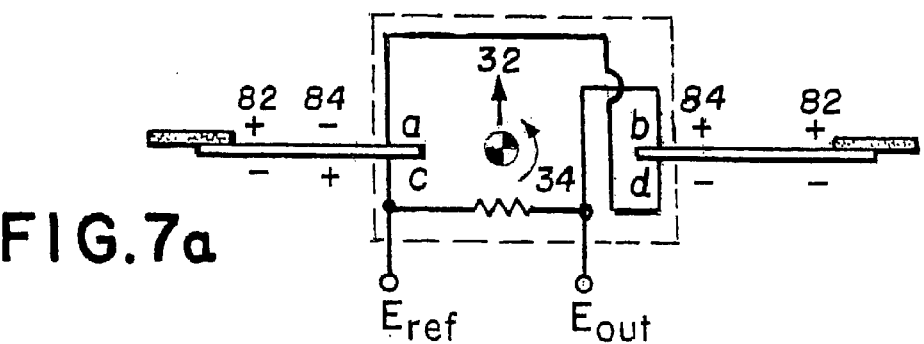
FIG. 7a is a side view of an alternate wiring arrangement of the motion sensor of FIG. 3.
Figure 7B:
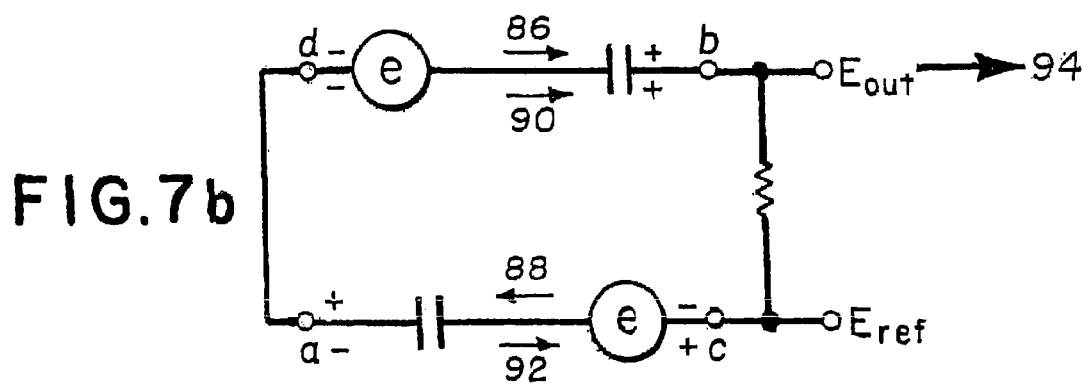

The second configuration of the preferred embodiment of the present invention shown in FIGS. 7a and 7b achieves the cancellation of RM and the preservation of TM. More particularly, and as shown in FIG. 7a, the wiring within module 44 provides for a connection of nodes a to d and b to c instead of the connection of a to b and c to d of FIG. 4b. The TM and RM polarities, 82 and 84 respectively, are shown with respect to the RM 34 and TM 32 composite movement. The equivalent circuit of the beam connections of FIG. 7a is shown in FIG. 7b. The resulting TM current flows 86 and 88, along with the resulting RM current flows 90 and 92 cancels RM and passes 2TM (94) or 86 plus 88 out through $E_{out}$.

Figure 8A:
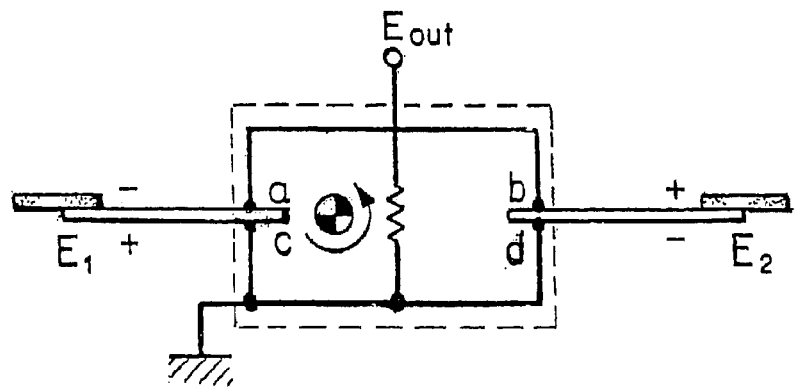
FIG. 8a is a side view of another alternate wiring arrangement of the motion sensor of FIG. 3.
Figures 8B, 9B:
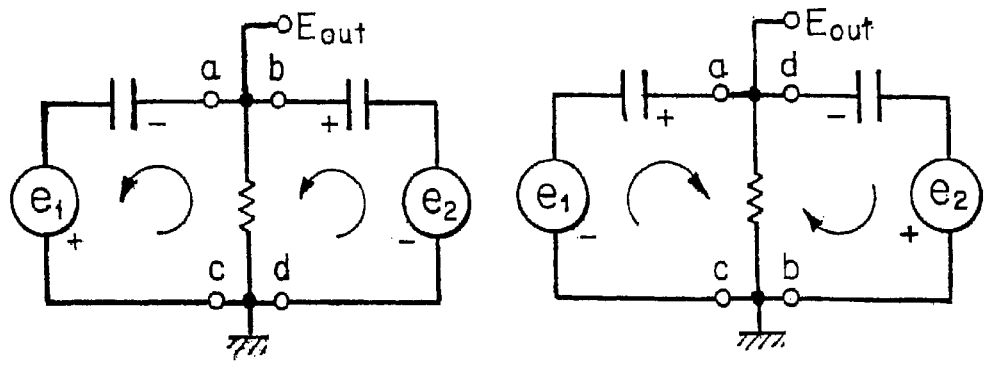
Figure 9A:
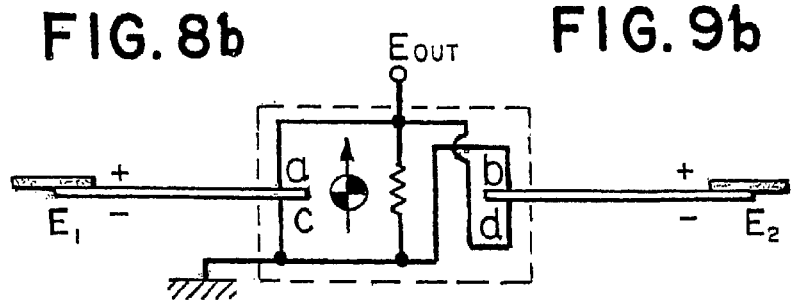
FIG. 9a is a side view of another alternate wiring arrangement of the motion sensor of FIG. 3.

The two preceding configurations have been circuits set up in "series". The next two configurations will depict the "parallel" set ups of the preferred embodiment of the present invention. Which configuration is chosen will depend upon individual preference and requirement of design. FIG. 8a illustrates a parallel circuit which will cancel RM. The equivalent circuit of FIG. 8a is shown in FIG. 8b. Similarly, FIG. 9a illustrates a parallel circuit which will cancel TM. The equivalent circuit of FIG. 9a is shown in FIG. 9b. The resulting polarity and current flows of these "parallel" configurations shall be determined and analyzed consistent with the preceding discussion of the "series" configurations.

Thus far, the preferred embodiment of the present invention has been described with the assumption that trimming and balancing the sensor near ideal could be accomplished during its fabrication. However, as this is not possible and/or overly expensive with current technology, we must deal with the inevitable differences between the beam pair. These differences effect the sensor in the form of a leakage of TM into the desired RM or a leakage of RM into the desired TM as the case may be. When one mode clearly dominates the other, as in, for example, the case of the subject riding in a road vehicle, the suppressed mode needs to be reduced 50 to 100 fold or more. This requires the active compensation of an electrical circuit, as discussed more particularly below.

Figure 10:
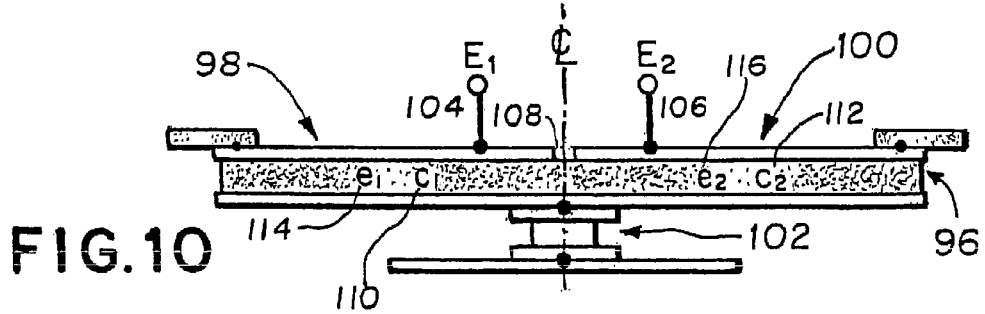
FIG. 10 is a side view of the balanced beam hook-up of the motion sensor of the preferred embodiment of the present invention.

Although four techniques have been discussed with respect to the ideal beam, only a single technique will be specified for the non-ideal beam hookup as it is the simplest preferred balancing circuitry. This non-ideal beam hook-up is shown in FIG. 10 and shall be referred to herein as a balanced beam. The ceramic material 96 of this balanced beam continues unbroken from beam 1(98) to beam 2(100). The material and construction of this interior layer electrically isolates the two ceramic halves because ceramic material is a very poor conductor. The composite beam behaves electrically as if there were two separate beams with their lower surfaces shorted together and fixed to a rigid mount 102, while the upper surfaces 104 and 106 ($E_1$ and $E_2$), while separated by break 108, are individually brought out for attachment to an external circuit.

This non-ideal balanced beam of FIG. 10 illustrates the source of two types of errors due to the inevitable differences between the beam pair. The first type is caused by differences in capacitance 110≠112 ($C_1 \neq C_2$), while the second is caused by differences in the magnitude of intrinsic voltages 114 or 116 ($e_1$ or $e_2$). If the beam halves were ideal, TM would yield $e_1 = e_2$ and RM would yield $e_1 = -e_2$. It will be understood that $e_1$ and $e_2$ (114 and 116) are intrinsically generated voltages not available for measurement because they are inside the beam, where $E_1$ and $E_2$ (104 and 106) are voltages that can be measured by external circuitry. Thus, if this new beam were to be moved, one would find that the measurable outputs $E_1$ and $E_2$, detected by an externally applied circuit, would generally be composed by both RM and TM influences. Therefore, if a simple resistor were tried in this non-ideal configuration to cancel TM, as it did in the previously discussed ideal configuration, it would fail to do so.

The error caused by differences in capacitance is a frequency dependent error. While the error caused by differences in the magnitude of intrinsic voltages (a scaling error between the beam halves comprised of a combination of a force/voltage coefficient, mass imbalance and mass spacing) is a frequency independent error. Although the frequency dependant capacitance error becomes less important with increasing frequency, it does not reduce this error to an insignificant amount. However, the scaling error can be trimmed electrically or physically by abrading the mass on the "heaviest" side.

Figure 11:
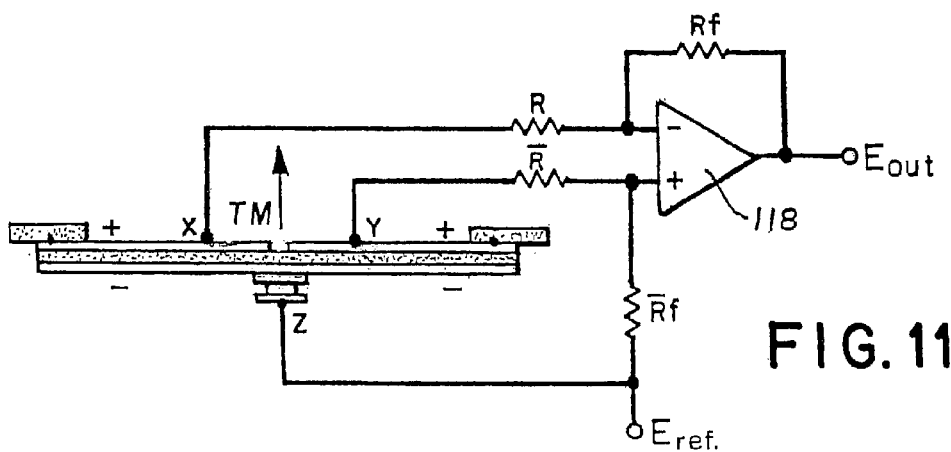
FIG. 11 is an electrical balancing circuit of FIG. 10.
Figure 12:
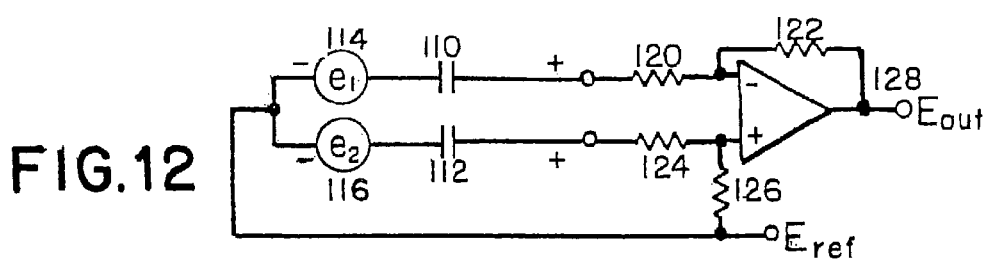
FIG. 12 is the circuit of FIG. 11 with the beam replaced by its equivalent circuit.

FIG. 11 illustrates the beam electrically hooked up to a differential amplifier 118. By replacing the beam with its equivalent circuit, the combined circuit of FIG. 12 results. The remaining Figures and the following discussion will be directed to TM because of the aforementioned immediate practical requirement of sleep determination in a moving vehicle. It will be understood that the present invention shall not be limited thereto, but has been chosen for discussion purposes. Furthermore, it is appreciated that one skilled in the art could utilize the differential amplifier (diff-amp.) circuit and direct the invention to RM.

Balance across any bandwidth can only be achieved if both types of error are frequency independent. For any set of values for R(120), $R_f$(122), $\overline{R}$(124) and $\overline{Rf}$(126) that do not meet the balance criteria (established below), the suppression properties of the circuit will be frequency dependent. Beam imbalance is functionally related to $E_{out}$(128), and as such can be precisely expressed with a mathematical expression derived by applying operational amplifier (op-amp) theory to the circuit of FIG. 12. The equation is shown below where $\omega j$=complex frequency.

$$E_{out} = \left[\frac{1 + C_1(R + Rf)\omega j}{1 + C_2(\overline{R} + \overline{Rf})\omega j}\right] \times \frac{\overline{Rf}\, C_2 e_2 \omega j}{1 + C_1 R \omega j} - \frac{Rf\, C_1 e_1 \omega j}{1 + C_1 R \omega j}$$

Note that the quantity within the square brackets can be made equal to 1 (one) if the two time constants $C_1(R+Rf)$ and $C_2(\overline{R}+\overline{Rf})$ are made equal. In other words, the time constants of the upper branch and lower branch of the diff-amp circuit must be made equal. If so, the above equation reduces to:

$$E_{out} = \frac{[\overline{R}_f C_2 e_2 - R_f C_1 e_1] \times \omega j}{(1 + C_1 R \omega j)}$$

Due to scaling errors, $e_1 \neq e_2$ for TM and generally differs up to ±10%. This difference can be modeled by assigning $e_1 = \epsilon_1 e_2$ where $\epsilon_1$ is a positive number between 0.9 and 1.1. (Note, for an ideal beam $\epsilon_1 = 1$). Similarly, $C_1 \neq C_2$ for TM and generally differs up to ±10%. Again, this difference can be modeled by assigning $C_1 = \epsilon_2 C_2$ where $\epsilon_2$ varies between 0.9 and 1.1. When $e_1 = \epsilon_1 e_2$ and $C_1 = \epsilon_2 C_2$ are substituted into the numerator of the above equation, the result is:

Numerator=$e_2 \, C_2 [\overline{R}_f - \epsilon_1 \, \epsilon_2 \, R_f] \omega j$ By factoring $e_2 \, C_2$ from the square bracketed items, exact cancellation is possible if:

$\overline{R}_f = \epsilon_1 \, \epsilon_2 \, R_f$

Therefore, if these calibrations can be performed, the numerator of the simplified equation is made equal to zero which will guarantee that $E_{out} = 0$ and thus cancel TM.

To summarize this mathematical analysis, first one resistor R or $R_f$ is adjusted so that $C_1(R+R_f) = C_2(\overline{R}+\overline{R}_f)$. Then one resistor $\overline{R}$ or $\overline{R}_f$ is adjusted so that $\overline{R}_f = \epsilon_1 \, \epsilon_2 \, R_f$. The diff-amp of FIG. 12 will now cancel (or suppress) common mode TM, and pass RM which will have a magnitude proportional to $2e_r$.

Although it was asserted that $C_1$ and $C_2$ would be equalized followed by scale corrections to the intrinsic voltages $e_1$ and $e_2$, capacitance error is still present. However, capacitance error $\epsilon_1$ and scale error $\epsilon_2$ combine in a multiplicative way, $\epsilon_1 \times \epsilon_2$, which produces a kind of "super" scale error that can still be trimmed away.

In order to perform these calibrations, the circuit parameter values need to be determined, i.e. resistance and capacitance. However, there is not an easily observable output from the diff-amp signifying that the time constants are balanced. Direct measurement of the values is not possible because the circuit elements and the op-amp itself interfere with measurement equipment such as voltmeters or capacitance meters. Balancing adjustments must occur after all physical operations, soldering, gluing, etc. have been accomplished. Essentially, the circuit board and all components for a given product must be assembled and tested before it is possible to balance the beam with the diff-amp. Thus, all adjustments must be performed while the circuit is powered up thereby using the diff-amp to empirically indicate when the beam halves are balanced for both error types. This can be accomplished, in one embodiment, by the circuit shown in FIG. 13.

Figure 13:
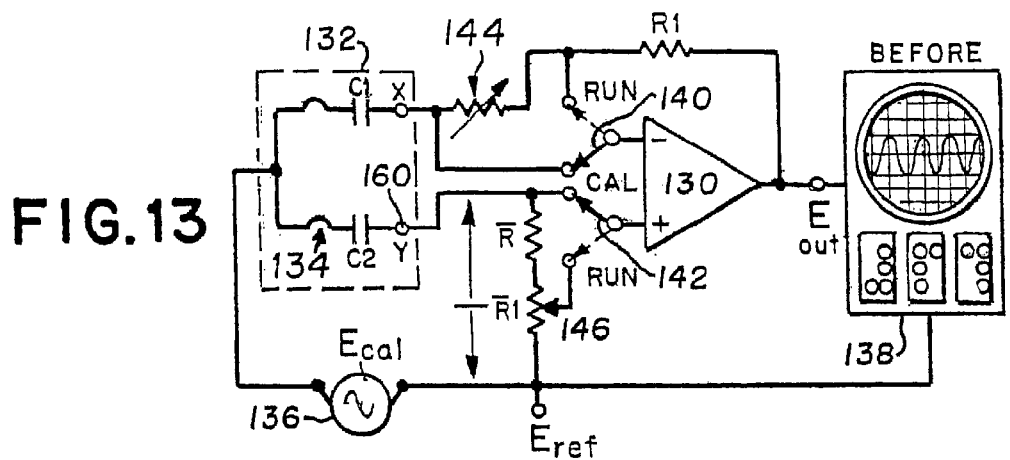
FIG. 13 is the circuit of FIG. 12 including additional balancing circuitry.

The circuit of FIG. 13 incorporates one op-amp 130. The dotted rectangular module 132 indicates that the enclosed beams are not moving. Without movement, the beams produce no voltage and, as a voltage source has zero resistance, $e_1$ and $e_2$ are modeled by jumper wires 134. Voltage is supplied by an externally applied precisely controlled signal generator $E_{cal}$(136). A stylized oscilloscope 138 is included to show that common mode voltage from the generator is usually not canceled by the diff-amp before adjustments have been made. Two switches 140 and 142 are provided that are either in the "Cal" position or "Run" position. This arrangement produces a workable method of adjusting the circuit so that the two time constant will be equal. Equality can be accomplished by adjusting variable resistor R(144). While scaling correction is accomplished by the voltage divider 146 found in the lower circuit branch which sets the correct ratio $\overline{R}/\overline{R}_f$.

Figure 14:
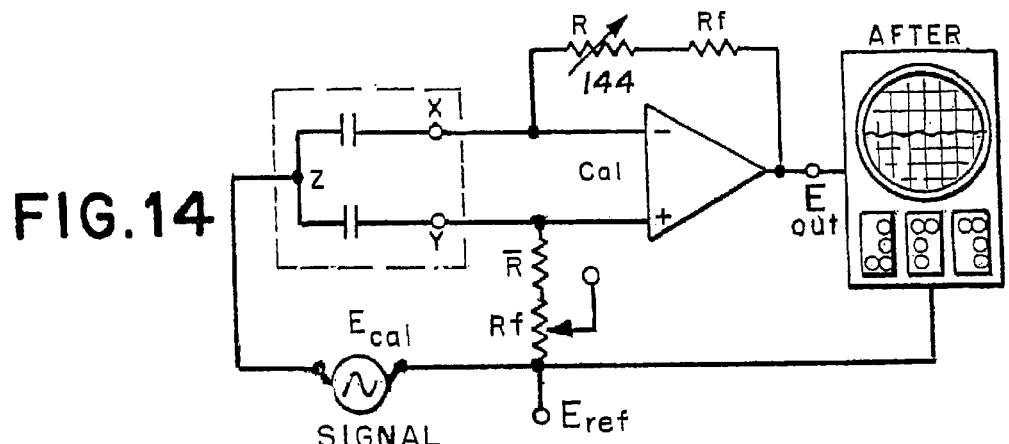
FIG. 14 is the equivalent circuit of FIG. 13 in the calibrate mode.

When the switches 140 and 142 of the circuit of FIG. 13 are in the "Cal" or calibrate mode, the electrically equivalent circuit of FIG. 14 is produced. In this configuration, $E_{out}$ is uniquely related to $E_{cal}$ and the circuit components $C_1$, $C_2$, R, $R_f$, $\overline{R}$ and $\overline{R}_f$ by the following equation:

$$E_{out}[C_1(R+R_f)-C_2(\overline{R}+\overline{R}_f)]\omega j \; E_{cal}$$

Not that (as desired) $E_{out}$ will be zero if $C_1(R+R_f)=C_2(\overline{R}+\overline{R}_f)$. This result is independent of frequency "$\omega$" and the amplitude of $E_{cal}$. After variable resistor 144 is correctly adjusted up or down from its midrange (midrange corresponding to ideal beams) $E_{out}$ will be equal to $E_{ref}$.

Figure 15:
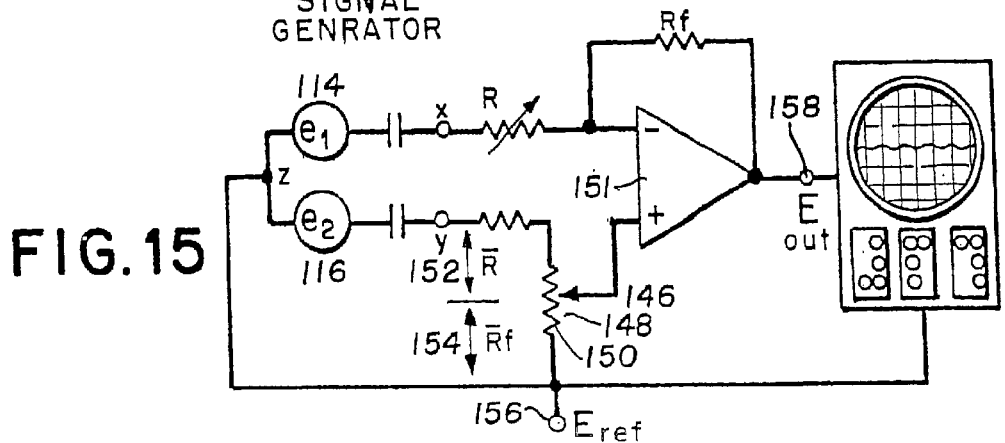
FIG. 15 is the equivalent circuit of FIG. 13 in the run mode.

When the switches 140 and 142 of the circuit of FIG. 13 are in the "Run" or run mode, the electrically equivalent circuit of FIG. 15 is produced. This circuit illustrates the removal of the dotted module 132 and signal generator 136 of FIG. 13 while reinserting the beam induced voltages 114 and 116 and more accurately depicting the voltage divider. Note that as the wiper 148 moves up or down the potentiometer resistance element 150, the lower branch time constant does not change. This is because the "+" input of the op-amp does not conduct current.

Additionally, $\overline{R}$(152) is the sum of a fixed resistor and a portion of the potentiometer, while $\overline{R}_f$(154) is only a portion of the available potentiometer resistance measured from the op-amp "+" input to $E_{ref}$(156), with the maximum resistance being the full value of the potentiometer. Therefore, by adjusting $\overline{R}_f$ up or down from its nominal center position (as would exist for ideal beams) one can increase or decrease the effective output $e_2$(116) which appears differentially with $e_1$(114) at the output $E_{out}$(158).

Intrinsic voltages $e_1$ and $e_2$ can be induced by any method that does not produce rotation. In the preferred embodiment, however, a small amplitude shaker table is used. This method is trial and error as one does not know initially which way to turn the scaling potentiometer. In particular, the shaker is turned off while adjustments are made then turned back on to observe the results on the oscilloscope 138.

Once calibration is complete, the circuit will pass RM and suppress TM. In order to cancel rotation and preserve translational motion an inverter is placed in either but not both beam diff-amp branches since an ideal inverter shifts its input by 180° or inverts it. Thus, the simplified equation can be stylized as:

(TM+RM)−(TM−RM)=2RM

Then, by placing an inverter in one of the circuit branches of FIG. 13, for example between point "y" (160) and the adjacent capacitor plate, the above equation changes to:

(TM+RM)+(TM−RM)=2TM

While particular embodiments of the invention have been shown and described, it will be obvious to those skilled in the art that changes and modifications may be made therein without departing from the invention in its broader aspects, and, therefore, the aim of the appended claims is to cover all such changes and modifications as fall within the true spirit and scope of the invention.

I claim:

1. A motion sensor for monitoring the activity of a body in motion, comprising:
   a mount;
   a pair of force detecting sensors capable of detecting both the magnitude and direction of an applied force, each of said sensors comprising:
   a beam having a first end, a second end, a top and a bottom, said beam rigidly attached to said mount generally near said first end; and
   said second end of said beam having a mass generally greater than said first end of said beam thereby providing a cantilever effect to said beam whereby when said sensor is put into general motion either said top or said bottom of said beam is stretched and produce both a voltage source effect and a capacitance effect, both of said effects corresponding to a translational motion component and a rotational motion component of said general motion; and
   a means for connecting said effects of said beams whereby said rotational component or said translational component is canceled.

2. A motion sensor for monitoring the activity of a body in motion as defined in claim 1 wherein said force detecting sensors are piezoelectric bimorph beams having a mass attached near said second ends of said beams.

3. A motion sensor for monitoring the activity of a body in motion as defined in claim 2 wherein each said beam is ceramic.

4. A motion sensor for monitoring the activity of a body in motion as defined in claim 1 wherein said means for connecting include a resistive element and associated circuitry.

5. A motion sensor for monitoring the activity of a body in motion as defined in claim 1 wherein each said sensor is further connected to a means to calibrate said effects.

6. A motion sensor for monitoring the activity of a body in motion as defined in claim 5 wherein said means to calibrate is a differential amplifier.

7. A motion sensor for monitoring the activity of a body in motion, comprising:
   a mount;
   a first and a second piezoelectric bimorph beam, each of said beams having a first end and a second end and a top and a bottom, said beams rigidly attached to said mount generally near said first ends;
   a mass attached generally near said second ends of said beams thereby providing a cantilever effect to said beams whereby when said sensor is put into general motion either said tops or said bottoms of said beams are stretched and produce both a voltage source effect and a capacitance effect, both of said effects corresponding to a translational motion component and a rotational motion component; and
   a resistive element connecting said effects of said beams whereby said rotational or said translational component is canceled.

8. A motion sensor for monitoring the activity of a body in motion as defined in claim 7 wherein each said beam is ceramic.

9. A motion sensor for monitoring the activity of a body in motion as defined in claim 7 wherein said sensor is further connected to a means to calibrate said effects.

10. A motion sensor for monitoring the activity of a body in motion as defined in claim 9 wherein said means to calibrate is a differential amplifier.

11. A method of making a motion sensor capable of suppressing a rotational or translational component from any general motion signal, consisting of:

provinding a mount;

providing a pair of force detecting sensors capable of detecting both the magnitude and direction of an applied force, each of said sensors comprising a beam having a first end, a second end, a top and a bottom;

attaching said beams to said mount generally near said first ends, said second ends of said beams having a mass generally greater than said first ends of said beam thereby providing a cantilever effect to said beams whereby when said sensor is put into general motion either said top or said bottom of said beam is stretched and produce both a voltage source effect and a capacitance effect, both of said effects corresponding to a translational motion component and a rotational motion component of said general motion; and attaching a means for connecting said effects of said beams whereby said rotational component or said translational component is canceled.

12. A method of making a motion sensor capable of suppressing a rotational or translational component from any general motion signal as defined on claim 11 further consisting of:

calibrating the sensor to reduce a difference in capacitance of the beams; and calibrating the sensor to reduce a difference in intrinsic voltage of the beams.

* * * * *